United States Patent [19]

Seiffert et al.

[11] Patent Number: 5,012,197

[45] Date of Patent: Apr. 30, 1991

[54] APPARATUS AND METHOD FOR DETERMINING THE RELATIVE PERCENTAGES OF COMPONENTS IN A MIXTURE

[76] Inventors: Volkhard Seiffert; Gerd Ihlenfeld; Klaus Bienert, all of Krausenstrasse 54A, D-3000 Hannover 1, Fed. Rep. of Germany

[21] Appl. No.: 337,051

[22] Filed: Apr. 12, 1989

[30] Foreign Application Priority Data

Apr. 19, 1988 [DE] Fed. Rep. of Germany ....... 3812959

[51] Int. Cl.$^5$ ............................................. G01N 27/02
[52] U.S. Cl. ..................................... 324/696; 324/717
[58] Field of Search ................................ 324/663–670, 324/672–675, 685–690, 693–698, 717, 65 P, 61 P

[56] References Cited

U.S. PATENT DOCUMENTS

| | | | |
|---|---|---|---|
| 2,695,976 | 11/1954 | Hasenkemp | 324/696 X |
| 3,992,665 | 11/1976 | Preikschat | 324/690 X |
| 4,053,825 | 10/1977 | Young | 324/469 |
| 4,063,153 | 12/1977 | Dechene et al. | |
| 4,074,184 | 2/1978 | Dechene et al. | 324/603 X |
| 4,107,599 | 8/1978 | Preikschat | 324/689 |
| 4,201,647 | 5/1980 | Spaziante et al. | 204/294 X |
| 4,347,478 | 8/1982 | Heerens et al. | 324/688 X |
| 4,427,426 | 1/1984 | Johnson et al. | 204/286 X |
| 4,489,278 | 12/1984 | Sawazaki | 324/452 X |
| 4,780,663 | 10/1988 | Mulder | 324/446 X |

FOREIGN PATENT DOCUMENTS

| | | | |
|---|---|---|---|
| 642640 | 1/1979 | U.S.S.R. | 324/65 P |
| 709177 | 5/1954 | United Kingdom | 324/61 P |

OTHER PUBLICATIONS

"Try Capacitance Transducers"; *Electronic Design;* Mar. 15, 1966; pp. 188–194; R. J. Levine.

Primary Examiner—Tom Noland

[57] ABSTRACT

An apparatus for determining the percentages of individual components of a mixture having at least two components of different electrical conductivities, the apparatus having at least two sensors connectable across an a.c. voltage source, and being arranged such that the mixture being introducible therebetween, wherein each sensor has a pin electrode having a first sensing surface for electrical contact with the mixture, and a plate electrode having a second sensing surface electrically insulated from the mixture, wherein the area of the second sensing surface is larger than the area of the first sensing surface; the pin electrode and the plate electrode of each sensor are each connected to the same potential of the voltage source.

11 Claims, 1 Drawing Sheet

APPARATUS AND METHOD FOR DETERMINING THE RELATIVE PERCENTAGES OF COMPONENTS IN A MIXTURE

BACKGROUND OF THE INVENTION

The present invention relates to an analysis device for determining the relative percentages of various components within a mixture which includes at least two components having different electrical conductivities. More particularly, the invention concerns analysis devices of the type including at least two electrodes of different polarities which are connectable across an a.c. source, wherein the mixture is introduced between the electrodes for analysis. The present invention also relates to a method employing a device for analysis of a mixture.

The control and monitoring of industrial processes utilizing mixtures of at least two components having different electrical conductivities, requires devices capable of determining the relative percentages, concentration and/or density of the different components. These devices can also be required for processes which utilize components in the same or different physical states. Such a determination can be accomplished in a known manner with devices which ascertain and evaluate the data on the electrical conductivity or the relative dielectric constant of a mixture.

An apparatus that can be employed for this purpose is disclosed in Dechene et al U.S. Pat. No. 4,074,184. The device described therein includes six capacitor electrodes disposed about the circumference of a tube in a mutually circumferentially offset arrangement. A special electrical circuit charges the electrodes from a single-phase high frequency voltage source. This apparatus measures the capacitance of a mixture flowing through a tube and is therefore limited to analysis of components of electrically non-conductive materials.

A further example is found in Dechene et al U.S. Pat. No. 4,063,153. This patent describes an apparatus composed of three pairs of elongate electrodes arranged about the circumference of a tube. The mixture, whose component percentages are to be determined, is guided through the tube between the pairs of electrodes. An electrical circuit is utilized to measure the electrical resistance of the mixture between the electrodes. The electrodes must be in electrical contact with the conductive mixture. Thus, this apparatus is used to measure the electrical conductivity of a mixture. In many cases this leads to unsatisfactory measuring results since the conductivity of a mixture may fluctuate within wide limits. For example, in a mixture of water and air, the air has a substantially lower conductivity than the water. If the mixing ratio varies between 0 and 100% air, the resolution of an electrical circuit for evaluation of the measured values must be sufficiently high so that it is able to measure the high conductivity of the water for a water content of about 100% as well as the low conductivity of the air for an air content of about 100%. Such a requirement cannot be met in a manner that is technologically practical or economical.

SUMMARY OF THE INVENTION

It is an object of the present invention to provide an apparatus with which the percentages of the components of a mixture composed of at least two components having different electrical conductivities can be measured in a simple manner and with great accuracy.

This object and others to become apparent as the specification progresses are accomplished by the invention, according to which, briefly stated, an apparatus for determining the percentages of individual components of a mixture having at least two components of different electrical conductivities includes at least two sensors connectable across an a.c. voltage source, the sensors being arranged such that the mixture is introducible therebetween. Each has a pin electrode with a first sensing surface for electrical contact with the mixture, and a plate electrode with a second sensing surface electrically insulated from the mixture, wherein the area of the second sensing surface is larger than the area of the first sensing surface. The pin electrode and the plate electrode of each sensor are each connected to the same potential of the voltage source.

With the apparatus of the present invention, it is possible to detect the electrical conductivity as well as the electrical capacitance of a mixture. The apparatus is therefore suitable for any desired mixture whose conductivity may fluctuate within wide limits. Its structure is simple since only one pin electrode and one plate electrode are required for each sensor. Due to the small surface area of the pin electrode compared to the plate electrode, the value measured between pin electrodes corresponding to conductivity is limited while the capacitive component of the current measured between plate electrodes results in a relatively high measured value. Both measured values can therefore be compiled easily and accurately. Thus, an electrical evaluation circuit can be employed which yields a technologically practical measuring range and measured value resolution.

For the physically correct evaluation of the resulting electrical measurement signal and the subsequent determination of the component percentages and thus their concentrations and densities, it may be necessary to shield the electrodes against undesirable extraneous influences resulting from the specific localized conditions at the measuring location. For this purpose, further embodiments of the invention are described wherein the pin electrodes and/or the plate electrodes are provided with shields on all sides which are electrically insulated from the associated other electrodes. The shield surrounding the plate electrode prevents propagation of the electrical field of the plate electrode to adjacent electrodes. Such a shield thus also permits the arrangement of a plurality of sensors in close proximity without interference. In view of the fact that the potential in the insulating material covering the plate electrode is, due to the electric losses therein, lower than the potential of the non-insulated pin electrode through which the ohmic part (resistance component) of the measuring current flows in case of an electrically conductive mixture, it is feasible to surround the pin electrode by a non-insulated shield.

This arrangement prevents the measuring current from flowing, through a film of moisture on the apparatus wall, to the complementary electrode in case the walls of the apparatus become wet.

DESCRIPTION OF THE PREFERRED EMBODIMENTS

Figure 1:
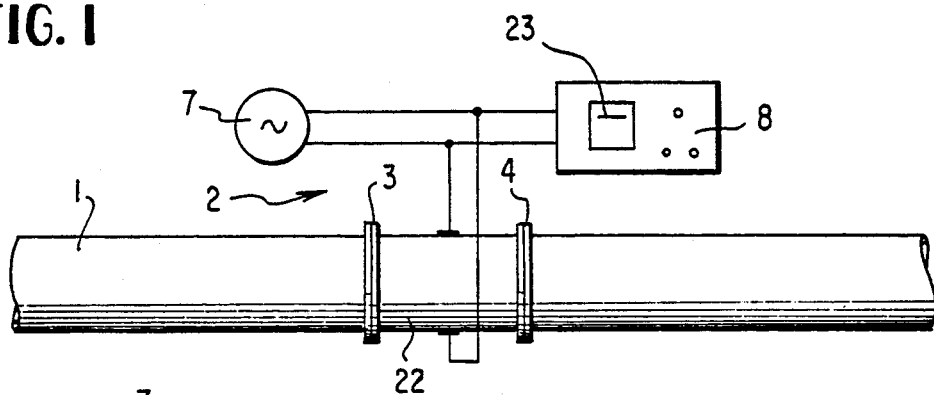
FIG. 1 is a side elevational view of a tubular conduit incorporating the invention.
Figure 2:
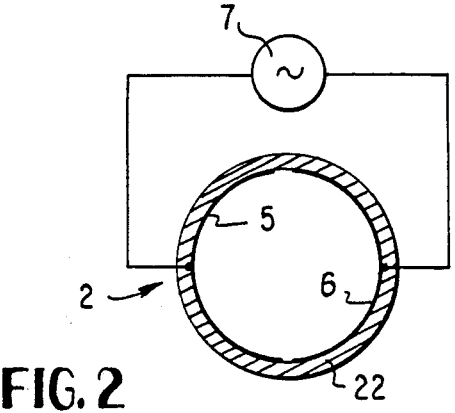
FIG. 2 is a schematic cross-sectional view of a first preferred embodiment of the invention.
Figure 3:
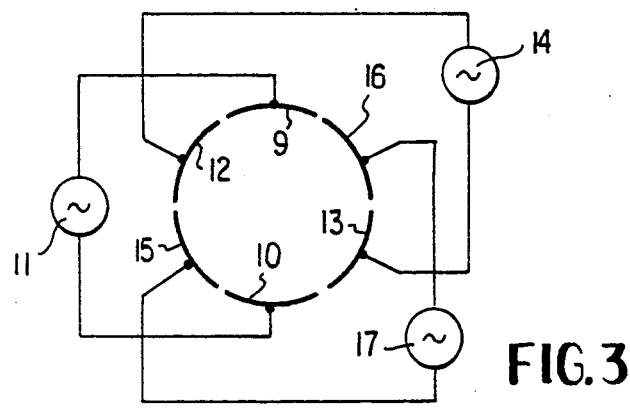
FIG. 3 is a schematic cross-sectional view of a second preferred embodiment of the invention.

FIG. 1 illustrates a section of a tubular conduit 1, in which there is installed an apparatus 2, two embodiments of which are shown in more detail in FIGS. 2 and 3. The apparatus 2 can be employed to determine the relative component percentages of a mixture which includes at least two components having different electrical conductivities and which flows through tubular conduit 1, passing through the apparatus 2. As shown in FIG. 1, the apparatus 2 has a conduit section 22 which is built into tubular conduit 1, for example, by means of flanges 3 and 4.

As illustrated in FIG. 2, the apparatus 2 has at least two sensors (also referred to hereafter as sensor electrodes or sensor electrode assemblies) 5 and 6 positioned within the conduit section 22 along the interior wall thereof. The electrodes 5 and 6 are connected across an a.c. voltage source 7 and are supplied with opposite polarities. The two electrodes 5 and 6 combined should cover the interior face of the conduit section 22 as completely as possible in the circumferential direction. The sensor electrodes 5 and 6 are connected with a measuring device 8 for measuring the current flow between the sensor electrodes 5 and 6. The measuring result is fed to a display device 23 of the measuring device 8.

The sensor electrodes of the apparatus need not be disposed in a tube or tubular section housing 22; they may be arranged in any desired configuration, as long as the two sensor electrodes of different polarities are so disposed that the mixture to be measured can be introduced between them.

Turning now to FIG. 3, in the preferred embodiment shown therein more than one pair of sensor electrodes is used in a tube section (housing), not shown in FIG. 3. The embodiment according to FIG. 3 comprises three sensor electrode pairs, formed, respectively, of sensor electrodes 9, 10; 12, 13; and 15, 16. The electrodes are offset relative to one another in the circumferential direction. Each sensor electrode pair is connected across a common a.c. voltage source; thus, electrodes 9 and 10 are connected across a.c. voltage source 11, electrodes 12 and 13 across a.c. voltage source 14 and electrodes 15 and 16 across a.c. voltage source 17. The voltage of the a.c. voltage sources may have a value of 10 V at a frequency up to 100 kHz. The six electrodes of such a device are each fed from voltage sources 11, 14 and 17 with a phase shift of 60° between the sources.

Each sensor electrode 5, 6, 9, 10, 12, 13, 15 and 16 of FIGS. 2 and 3 may be constructed according to any of the alternative principles of construction illustrated in FIGS. 4, 5 and 6, and described below.

According to the present invention, each sensor electrode is an electrode assembly, comprised of a small-area pin electrode 18 and a plate electrode 19. The plate electrode 19 has a large surface area compared to the surface area of the pin electrode 18. Pin electrode 18 and plate electrode 19 are either made of one piece or they are electrically insulated from one another, for example, by an air gap as they are supported by a wall. In either instance, the pin electrode and the plate electrode of the same sensor electrode assembly are connected to the same potential. The pin electrode 18 is arranged in such a manner that, during operation of the apparatus, it is in electrical contact with the mixture to be analyzed. In contrast thereto, plate electrode 19 is electrically insulated from the mixture by an electrically insulating coating provided at least on the exposed front surface of the plate electrode 19.

Figure 4:
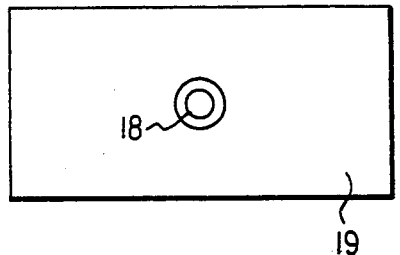
FIG. 4 is a plane view of the exposed surface of a first embodiment of a sensor of the invention.
Figure 5:
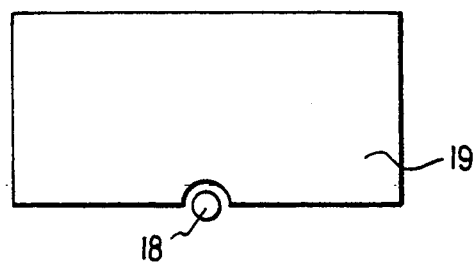
FIG. 5 is a plane view of the exposed surface of a second embodiment of a sensor of the invention.

According to FIG. 4, the pin electrode 18 is disposed in an opening in plate electrode 19 in the center thereof. In the variant shown in FIG. 5, the pin electrode 18 is arranged at an edge of the plate electrode 19, in a lateral recess thereof. The outer end of the pin electrode 18 may be flush with the face of the plate electrode 19 or may project slightly therebeyond.

Figure 6:
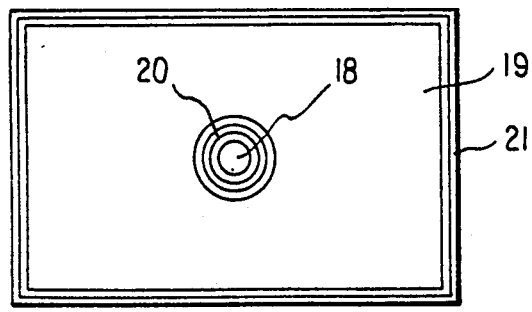
FIG. 6 is a plane view of the exposed surface of a third embodiment of a sensor of the invention.

To ensure that the measuring results are not affected by structural conditions and external influences, pin electrode 18 and plate electrode 19 are preferably provided with conductive shields 20 and 21 respectively, as illustrated in FIG. 6. Shield 20 surrounds and is electrically insulated from pin electrode 18 and, during operation of the apparatus, shield 20 is in electrical contact with the mixture as is pin electrode 18. Shield 21 surrounds laterally the plate electrode 19 and is electrically insulated therefrom and from the mixture by an electrically insulating material on its surface. Shields 20 and 21 ensure that the fields generated between the electrode assemblies of one assembly pair do not extend to adjacent pairs, but are positively directed to the respectively other assembly of the same pair. The shields 20 and 21 each lie at the same potential as the pin electrode 18 and the plate electrode 19. It is feasible to so design the sensor electrode assemblies that either only the plate electrode 19 is provided with a shield 21 or only the pin electrode 18 is provided with a shield 20.

In the description which follows, the use and operation of the described apparatus will be set forth.

After installing the apparatus, for example, in a tubular conduit 1 as illustrated in FIG. 1, the apparatus is calibrated. For this purpose, the individual components of a mixture are initially guided separately between the sensor electrode assemblies. A.C. is applied across the sensors and measurements are taken. For example, if a water/air mixture is to be analyzed, water is guided through the apparatus first, with its temperature being raised. The measurements obtained are then analyzed to calibrate the apparatus. In the same manner, air is then passed through the conduit 1 at increasing pressure, and calibration is performed. A curve obtained from the calibration then corresponds to the upper and lower limit values of the pure components. The values measured by the apparatus during normal operation for analysis of a water/air mixture lie between the curve for water, on the one hand, and the curve for air, on the other hand. For measuring the current flowing between the two pin electrodes 18 of an electrode assembly pair an ammeter circuit is provided which includes the two pin electrodes, while for measuring the electric charge between the two plate electrodes 19 of the same electrode assembly pair a voltmeter circuit is provided which includes the two plate electrodes 19 and measures the potential difference therebetween. Additionally, for a quantitative evaluation of the measuring results, temperature and/or pressure of the mixture are also monitored during the normal operation procedure.

It will be understood that the above description of the present invention is susceptible to various modifications, changes and adaptations, and the same are intended to be comprehended within the meaning and range of equivalents of the appended claims.

What is claimed is:

1. In an apparatus for determining the percentages of individual components of a mixture having at lest two components of different electrical conductivities, said apparatus including at least two sensors connectable across an a.c. voltage source, and being arranged such that the mixture is introducible therebetween, the improvement wherein each sensor comprises:
   a pin electrode having a first sensing surface for electrical contact with said mixture, and
   a plate electrode having a second sensing surface, said plate electrode being electrically insulated from said mixture, wherein
   the area of said second sensing surface is larger than the area of said first sensing surface;
   said pin electrode and said plate electrode of each sensor are each connected to the same potential of said voltage source.

2. An apparatus according to claim 1, further including:
   a plurality of shields, each shield surrounding a respective one of said pin electrodes about a perimeter of said first sensing surface, and being connected to the same potential as said respective pin electrode; each said shield being electrically insulated from said respective pin electrode and having an exposed surface for contact with said mixture.

3. An apparatus according to claim 1, further including:
   a plurality of shields, each shield surrounding a respective one of said plate electrodes about a perimeter of said second sensing surface and being connected to the same potential as said respective plate electrode; each shield being electrically insulated from said respective plate electrode, and from said mixture.

4. An apparatus as defined in claim 1, wherein each of said pin electrodes and said plate electrodes are surrounded about the perimeter of said first and second sensing surfaces by a shield which is electrically insulated from the electrode it surrounds.

5. An apparatus as defined in claim 1, wherein each pin electrode is disposed in an opening extending through said second sensing surface.

6. An apparatus as defined in claim 5, wherein said opening is disposed in the center of said second sensing surface 7. An apparatus as defined in claim 1, wherein said pin electrode is disposed outside said plate electrode.

8. An apparatus as defined in claim 1, wherein said sensors are disposed in a section of a tubular conduit, said sensors substantially covering an annular portion of the inner surface of said conduit section.

9. An apparatus as defined in claim 1, wherein six sensors are disposed within a section of a tubular conduit evenly spaced about an annular portion of said section, every two mutually diametrically oppositely disposed electrodes having opposite polarities and being connected across a common voltage source.

10. An apparatus according to claim 1, further including:
    a plurality of shields, each shield being disposed around a respective one of the pin electrodes and being spaced apart from the respective one of the pin electrodes.

11. An apparatus according to claim 10, wherein each shield is cylindrical and is mounted coaxial to the respective one of the pin electrodes.

* * * * *